United States Patent [19]

Kim

[11] Patent Number: 5,294,722

[45] Date of Patent: Mar. 15, 1994

[54] PROCESS FOR THE PREPARATION OF IMIDAZOLES USEFUL IN ANGIOTENSIN II ANTAGONISM

[75] Inventor: Kyoung S. Kim, Lawrenceville, N.J.

[73] Assignee: E. R. Squibb & Sons, Inc., Princeton, N.J.

[21] Appl. No.: 869,971

[22] Filed: Apr. 16, 1992

[51] Int. Cl.$^5$ ............... C07D 235/30; C07D 235/04; C07D 233/54; C07D 233/00
[52] U.S. Cl. ................................. 548/251; 548/255; 548/306.1; 548/112; 548/113; 548/266.2; 548/266.4; 548/210; 548/215; 544/139; 544/370; 546/210; 564/258
[58] Field of Search ............... 548/336, 337, 113, 112, 548/327, 253, 255, 266.2, 266.4, 215, 341, 342, 334.5; 544/370, 139; 546/210

[56] References Cited

U.S. PATENT DOCUMENTS

| | | | |
|---|---|---|---|
| 4,207,324 | 6/1980 | Matsumura et al. | 548/336 |
| 4,340,598 | 7/1982 | Furukawa et al. | 548/337 |
| 4,355,040 | 10/1982 | Furukawa et al. | 548/342.1 X |
| 4,582,847 | 4/1986 | Furukawa et al. | 514/400 |
| 4,632,934 | 12/1986 | Iizuka et al. | 548/342.1 X |
| 4,812,462 | 3/1989 | Blankley et al. | 514/303 |
| 4,816,463 | 3/1989 | Blankley et al. | 548/337 |
| 4,820,843 | 4/1989 | Aldrich et al. | 548/337 |
| 4,826,990 | 5/1989 | Musser et al. | 548/337.1 X |
| 4,832,732 | 5/1989 | Lutz et al. | 548/337.1 X |
| 4,859,684 | 8/1989 | Raeymaekers et al. | 548/327 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,117,004 | 5/1992 | Kempe et al. | 548/337 |
| 5,126,342 | 6/1992 | Chakravarty et al. | 548/337.1 X |

FOREIGN PATENT DOCUMENTS

| | | | |
|---|---|---|---|
| 0253310 | 1/1988 | European Pat. Off. | 548/335.1 |
| 0323841 | 7/1989 | European Pat. Off. | 548/335.1 |
| 0324377 | 7/1989 | European Pat. Off. | 548/335.1 |
| 0429257 | 5/1991 | European Pat. Off. | 548/335.1 |
| 0434249 | 6/1991 | European Pat. Off. | 549/462 |

OTHER PUBLICATIONS

Akagana et al., Chemical Abstracts, vol. 80, #28443x (1974).
Cotton et al., Chemical Abstracts, vol. 79, #197965k (1978).
Mamalis et al., Chemical Abstracts, vol. 79, #42507g (1973).
Ochiai et al., Chemical Abstracts, vol. 90, #87483q (1979).
Scheinbaum et al., Tetrahedron Letters, No. 24, pp. 2205–2208 (1971).
O. Diels, Berichte, 52, 43 to 51 (1919).
O. Diels, Berichte, 51, 965 to 976 (1918).

*Primary Examiner*—Floyd D. Higel
*Attorney, Agent, or Firm*—John M. Kilcoyne

[57] ABSTRACT

Imidazoles of the formula

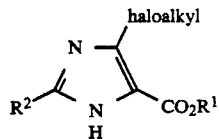

are prepared by treating a ketone

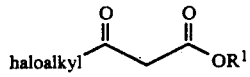

with a nitrogenic acid, nitrite or nitrate in the presence of an acid to form a hydroxynitrile

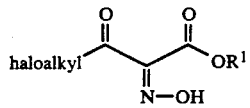

which is treated with $R^2$—CHO and an ammonium to form an N-hydroxyimidazole (Abstract continued on next page.)

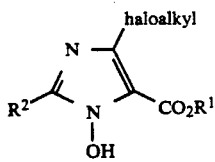

which is reduced in the presence of a buffer. In these compounds, $R^1$ is hydrogen, alkyl, haloalkyl, cycloalkyl, cycloalkylalkyl, aryl or aralkyl;

$R^2$ is alkyl, alkenyl, alkynyl, cycloalkyl, cycloalkylalkyl, cycloalkylalkenyl, cycloalkylalkynyl, or —$(CH_2)_m Z(CH_2)_n R^3$, each of which is optionally substituted with F or —$CO_2R^1$; or aryl or aralkyl, each of which is optionally substituted with 1 or 2 groups selected from halogen, lower alkoxy, lower alkyl, or nitro;

$R^3$ is hydrogen, alkyl, cycloalkyl, lower alkenyl, or lower alkynyl;

and the remaining symbols are as defined in the specification.

19 Claims, No Drawings

PROCESS FOR THE PREPARATION OF IMIDAZOLES USEFUL IN ANGIOTENSIN II ANTAGONISM

FIELD OF THE INVENTION

This invention relates to Angiotensin II antagonists, intermediates thereof and processes of preparation therefor.

DESCRIPTION OF THE INVENTION

Imidazoles of the formula

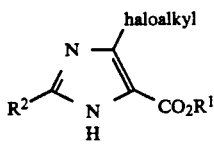   I are useful intermediates in the preparation of angiotensin II antagonists. See, e.g., U.S. patent application Ser. No. 838,492, filed Feb. 7, 1992 and European patent application 323,841 (Dupont). The symbols in compound I are defined as follows:

$R^1$ is hydrogen, alkyl, haloalkyl, cycloalkyl, cycloalkylalkyl, aryl or aralkyl;

$R^2$ is alkyl, alkenyl, alkynyl, cycloalkyl, cycloalkylalkyl, cycloalkylalkenyl, cycloalkylalkynyl, or $-(CH_2)_m Z(CH_2)_n R^3$, each of which is optionally substituted with 1 or 2 groups selected from halo and $-CO_2R^1$; or aryl or aralkyl, each of which is optionally substituted with 1 or 2 groups selected from halogen, lower alkoxy, lower alkyl, and nitro;

$R^3$ is hydrogen, alkyl, cycloalkyl, lower alkenyl, or lower alkynyl;

Z is O, $NR^4$, or S;

$R^4$ is hydrogen, alkyl, cycloalkyl, aryl, cycloalkylalkyl, or aralkyl;

m is an integer from 0 to 5; and n is an integer from 1 to 5.

In accordance with the present invention, compound I is prepared as follows. A ketone

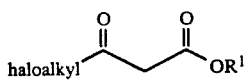   II is treated with a nitrogenic acid, nitrite or nitrate in the presence of an acid. Preferred reagents are nitric acid and alkali metal nitrites and nitrates, of which sodium nitrite is most preferred. Acetic acid is the preferred acid. Such treatment produces a hydroxynitrile

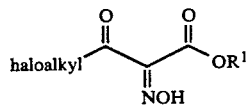   III which is then treated with an aldehyde

   IV and an ammonium (ammonia, an ammonium halide, or ammonium hydroxide) to form an N-hydroxyimidazole

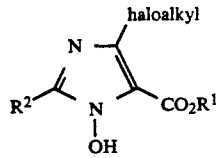   V

N-hydroxyimidazole V is treated with a reducing agent in the presence of a buffer to form compound I. Suitable reducing agents include titanium trichloride, zinc, and the like. Suitable buffers include sodium acetate, sodium phosphate, and the like. The preferred reducing agent is titanium trichloride; the preferred buffer, sodium acetate.

Compounds I and V may be used in a number of processes to prepare angiotensin II antagonists. For example, either may be coupled with a compound of the formula

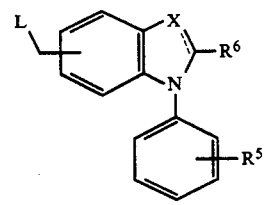   VI wherein the dashed line signifies that a double bond may be present, and wherein:

L is a leaving group, such as halogen;

X is N,

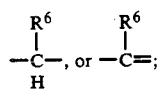

$R^5$ is hydrogen,

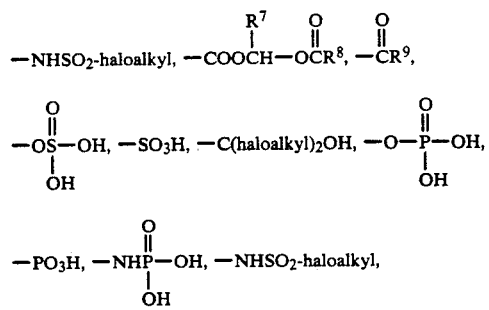

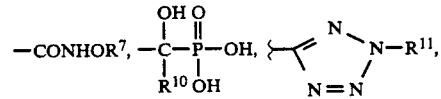

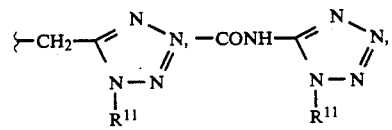

$-CONHNHSO_2$-haloalkyl,

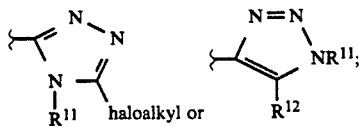

$R^6$ is hydrogen, halogen, haloalkyl, alkyl, aryl, cycloalkyl, cycloalkylalkyl, aralkyl, or

$R^7$ is hydrogen, alkyl, aryl, aralkyl, cycloalkyl, or cycloalkylalkyl;

$R^8$ is alkyl,

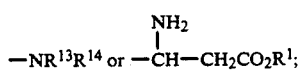

$R^9$ is hydrogen, cycloalkyl, $-(CH_2)_pC_6H_5$, $-OR^{11}$ or $-NR^{15}R^{16}$;

$R^{10}$ is hydrogen, alkyl, or phenyl;

$R^{11}$ is hydrogen, alkyl, cycloalkyl, aryl, aralkyl, a 5- to 7-membered carbocyclic ring that may have another 5- to 7-membered carbocyclic ring fused thereto,

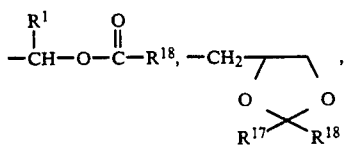

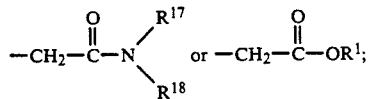

$R^{12}$ is $-CN$, $-NO_2$ or $-CO_2R^1$;

$R^{13}$ and $R^{14}$ are independently hydrogen, benzyl or together are alkylene or alkenylene, forming a 4- to 7-membered saturated, unsaturated or aromatic ring with the nitrogen atom to which they are attached;

$R^{15}$ and $R^{16}$ independently are hydrogen, alkyl, phenyl, benzyl, α-methylbenzyl, or together with the nitrogen atom to which they are attached form a ring of the formula

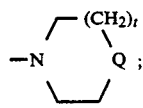

Q is $NR^7$, O or $CH_2$;

$R^{17}$ is hydrogen, alkyl, cycloalkyl, aryl or arylalkyl and $R^{18}$ is hydrogen, alkyl, cycloalkyl, aryl, arylalkyl or alkoxy, or together $R^{17}$ and $R^{18}$ are $-(CH_2)_2-$, $-(CH_2)_3-$, $-CH=CH-$ or

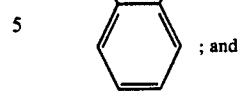

; and t is 0 or 1.

Compounds I or V may be coupled to compound VI by treatment with a coupling agent in an organic solvent to form an ester

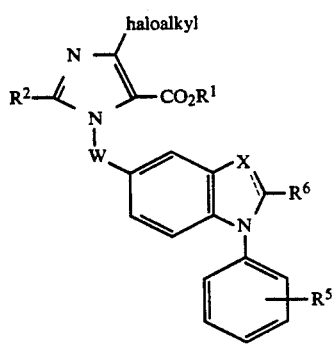

VII wherein W is $-CH_2-$ or $-O-CH_2-$. Suitable coupling agents are alkali metal alkylsilazanes (e.g., potassium hexamethyldisilazane), hydrides (e.g., sodium hydride), carbonates (e.g., sodium carbonate), bicarbonates (e.g., sodium hydrogen carbonate), and the like. Suitable organic solvents for the coupling reaction are tetrahydrofuran, dimethylformamide, and the like.

Aldehyde VII can thereafter be reduced to provide an alcohol

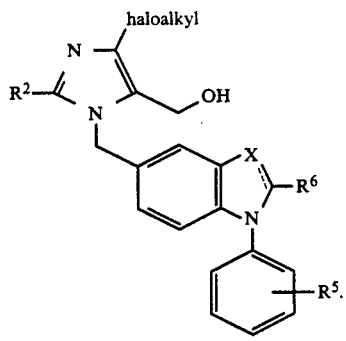

VIII

Suitable reducing agents include lithium aluminum hydride, lithium bis(ethoxymethoxy)aluminum hydride, sodium, lithium and zinc borohydride, and the like. Suitable solvents for the reduction include ethanol, tetrahydrofuran, and the like.

Alcohol VIII may then be alkylated or arylated to form

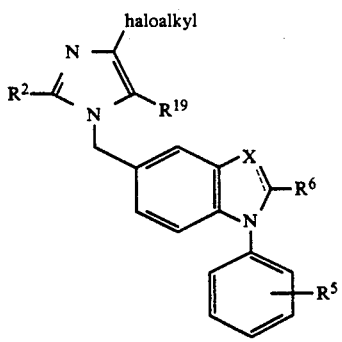

wherein:

R[19] is hydrogen; —CN; alkyl; haloalkyl; alkenyl; haloalkenyl; phenylalkenyl; —(CH$_2$)$_p$-imidazol-1-yl; —(CH$_2$)$_p$-1,2,3-triazolyl, optionally substituted with one or two groups selected from —CO$_2$R$^1$ and alkyl of 1 to 4 carbon atoms; —(CH$_2$)$_p$-tetrazolyl; —(CH$_2$)$_q$OR$^{20}$ other than —CH$_2$OH;

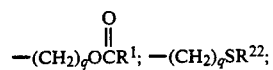

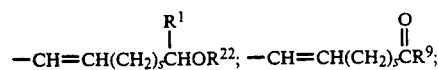

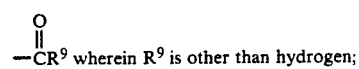

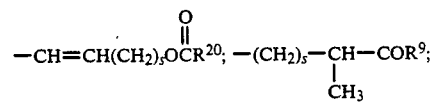

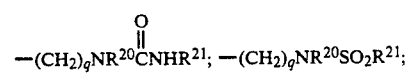

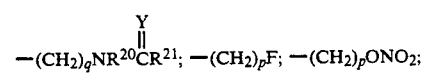

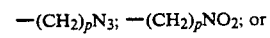

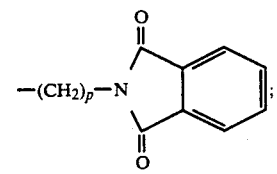

R$^{20}$ is hydrogen, alkyl, cycloalkyl, phenyl, or benzyl;
R$^{21}$ is alkyl, haloalkyl, 1-adamantyl, 1-naphthyl, 1-(1-naphthyl)ethyl, or —(CH$_2$)$_p$C$_6$H$_5$;
R$^{22}$ is hydrogen, alkyl, phenyl, benzyl, acyl, or phenacyl;
Y is O or S;
p is an integer from 1 to 10; and
q is an integer from 1 to 10; and
s is an integer from 0 to 5.

Alternatively, aldehyde VII is subjected to Wittig homologation to form compound IX. Compounds VII, VIII and IX are useful as angiotensin II antagonists, as described in U.S. Ser. No. 838,492, filed Feb. 7, 1992.

Listed below are definitions of terms used in this specification. These definitions apply to the terms as used throughout this specification, either individually or as part of a larger group, unless otherwise limited in specific instances.

The term "aryl" or "ar-" refers to unsubstituted phenyl and phenyl substituted with halogen, alkyl, alkoxy, alkylthio, hydroxy, alkanoyl, nitro, amino, dialkylamino, or trifluoromethyl groups. Unsubstituted and monosubstituted phenyl are preferred and unsubstituted phenyl is most preferred.

The term "alkyl" refers to straight or branched chain groups having 1 to 10 carbon atoms. The term "lower alkyl" refers to groups having 1 to 4 carbon atoms, which are preferred.

The terms "alkenyl" and "alkynyl" refer to straight or branched chain groups having 2 to 10 carbon atoms. Groups having 1 to 4 carbon atoms are preferred.

The terms "cycloalkyl" and "cycloalkenyl" refer to cyclic hydrocarbon groups having 3 to 8 carbon atoms.

The term "alkoxy" refers to straight or branched chain groups having 1 to 8 carbon atoms. The term "lower alkoxy" refers to groups having 1 to 4 carbon atoms, which are preferred.

The terms "halogen" and "halo" refer to fluorine, chlorine, bromine and iodine, with fluorine and chlorine preferred.

The terms "haloalkyl" and "haloalkenyl" refer to straight or branched chain groups of 1 to 4 carbon atoms substituted with one or more halogen atoms. The preferred haloalkyl groups are —CF$_3$ and —C$_2$F$_5$.

The term "acyl" refers to groups of the formula

wherein R is alkyl, aryl, cycloalkyl, cycloalkenyl, aralkyl, cycloalkylalkyl, and cycloalkenylalkyl. The preferred acyl group is alkanoyl, wherein R is alkyl.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH—, and —CH(C$_2$H$_5$)—CH=CH.

The invention will now be further described by the following working examples, which are illustrative rather than limiting.

EXAMPLE 1

2-Butyl-1-hydroxy-4-(trifluoromethyl)-1H-imidazole-5-methanol

A. 2-(Hydroxylmino)-3-oxo-4,4,4-trifluorobutanoic acid, ethyl ester

A solution of 20.0 g of sodium nitrite (0.29 mmol) in 35 mL of water was added dropwise over 50 minutes to a stirred, ice-cooled solution of 22.8 g of ethyl 4,4,4-trifluoroacetoacetate (0.12 mmol) in 30 mL of acetic acid. The reaction was continued for 2 hours, with gradual warming to 15° C. Water and acetic acid were removed under reduced pressure (azeotroped with toluene). The crude product was partitioned between ethyl acetate and saturated aqueous potassium hydrogen carbonate solution, the layers were separated, the ethyl acetate layer was washed with saturated aqueous potassium hydrogen carbonate solution, brine, dried over sodium sulfate, and concentrated to yield 21.4 g of compound A as a light yellow oil (81%), which upon standing slowly solidifies to a white, waxy solid.

$^{13}$C NMR (67.5 MHz, CDCl$_3$): d161.2, 146.0, 124.0, 119.4, 62.6, 13.9.

$^1$H NMR (270 MHz, CDCl$_3$): d 4.41–4.32 (m, 2H), 1.35 (t, 3H, J=7.0 Hz).

B. 2-Butyl-1-hydroxy-4-(trifluoromethyl)-1H-imidazole-5-carboxylic acid, ethyl ester A solution of 9.87 mL of valeraldehyde (92.9 mmol) in 150 mL of saturated ethanolic ammonia was cooled to 0° C. and added to 19.8 g (92.9 mmol) of compound A. The red-orange solution was stirred at 0° C. under an argon atmosphere for 30 minutes and subsequently at room temperature overnight. The solvent was removed under reduced pressure and co-evaporated with ether. The residue was dissolved in 150 mL of ether and 0.1 g of insoluble material was removed by filtration. Concentration of the filtrate under reduced pressure yielded 27.7 g of a light yellow-orange taffy. Flash chromatography on 750 g of silica gel eluting with 2 L of methylene chloride followed by 98:1:1 methylene chloride:-methanol:acetic acid yielded 9.8 g of compound B as a light yellow solid (38%).

Melting point: 77.5°–80.5° C.

C. 2-Butyl-1-hydroxy-4-(trifluoromethyl)-1H-imidazole-5-methanol

Solid lithium borohydride (0.15 g, 6.85 mmol) was added in several portions to an ice-cooled, stirred solution of 0.60 g compound B (2.14 mmol) in 21.3 mL of anhydrous tetrahydrofuran under an argon atmosphere. The reaction was continued for 1.5 hours at room temperature and subsequently for 3 hours at 65° C. Tetrahydrofuran was removed under reduced pressure. The residue was treated with 30 mL of saturated aqueous potassium hydrogen carbonate solution (added slowly, with the reaction vessel immersed in a 0° C. ice bath), and the suspension was stirred for 10 minutes at room temperature. The crude product was extracted with 2×30 mL of ethyl acetate, the combined ethyl acetate layers were washed with 2M trisodium citrate solution, brine, dried over sodium sulfate, and concentrated under reduced pressure to yield 0.25 g of a yellow taffy. The aqueous layer from the above extractions was brought to pH 7.0 by the addition of oxalic acid and extracted with 2×30 mL of ethyl acetate. The combined ethyl acetate layers were washed with brine, dried over sodium sulfate, combined with the 0.25 g of product obtained above and concentrated under reduced pressure to yield 0.53 g of a colorless taffy. Flash chromatography on 32 g of silica gel eluting with 98:2 methylene chloride:methanol yielded 0.37 g of Example 1 as a white glass (73%).

Melting point: 132°–135° C.

EXAMPLE 2

3'-[[[2-Butyl-5-(hydroxymethyl)-4-(trifluoromethyl)-1H-imidazole-5-yl]oxy]methyl][1,1'-biphenyl]-2-carboxylic acid, potassium salt A. 3'-[[[2-Butyl-5-(hydroxymethyl-4-(trifluoromethyl)-1H-imidazole-5-yl]oxy]methyl][1,1'-biphenyl]-2-carboxylic acid, ethyl ester A solution of 0.10 g of Example 1 (0.42 mmol) in 1.10 mL of dimethylformamide at room temperature was purged for 5 minutes with a stream of argon. 3'-(Bromomethyl)[1,1'-biphenyl]2-carboxylic acid, ethyl ester was added (0.13 g, 0.36 mmol, 85% purity), followed by 0.27 g of cesium carbonate (0.84 mmol). The reaction mixture was stirred for 2 hours and 10 minutes under an argon atmosphere. Dimethylformamide was removed under reduced pressure. The residue was flash-chromatographed on 10 g of silica gel eluting with 99.5:0.5 methylene chloride:methanol to yield 0.14 g of compound A as a viscous, colorless oil (70%).

$^{13}$C NMR (67.5 MHz, CDCl$_3$): δ 168.4, 145.3, 142.3, 141.5, 132.7, 131.3, 130.9, 130.6, 129.9, 138.6, 127.6, 82.4, 61.0, 51.6, 29.2, 25.6, 22.3, 13.6.

$^1$H NMR (270 MHz, CDCl3): δ 7.88 (dd, 1H, J=1.2 Hz, J=8.2 Hz), 7.58–7.49 (m, 1H), 7.46–7.27 (m, 6H), 7.44 (s, 1H), 5.31 (s, 2H), 4.70 (s, 2H), 4.10 (q, 2H, J=7.0 Hz), 2.61 (t, 2H, J=7.6 Hz), 1.76–1.64 (m, 2H), 1.42–1.28 (m, 2H), 1.03 (t, 3H, J=7.0 Hz), 0.93 (t, 3H, J=7.6 Hz).

B. 3'-[[[2-Butyl-5-(hydroxymethyl)-4-(trifluoromethyl)-1H-imidazole-5-yl]oxy]methyl][1,1'-biphenyl]-2-carboxylic acid, potassium salt A solution of 0.12 g of compound A (0.25 mmol) in 4.0 mL of methanol at room temperature under argon was treated with 0.13 mL of an aqueous 2.12M potassium hydroxide solution. The reaction mixture was stirred overnight. The reaction was subsequently heated at 65° C. for 9.25 hours. Methanol was removed under reduced pressure, the residue was dissolved in a minimal amount of water and passed through a column of HP-20 resin (1.0 cm I.D.×12 cm resin bed height) eluting with water (7×8 mL fractions) followed by 70:30 water:methanol. Lyophilization of pooled fractions yielded 60.1 mg of Example 2 as a white solid (49%) with no distinct melting point (Example 2 changed form at 100° C. and decomposed at 200° C.).

Analysis for C$_{23}$H$_{22}$F$_3$N$_2$O$_4$.K.0.88H$_2$O: Calc'd: C, 54.98; H, 4.77; F, 11.34; N, 5.58. Found: C, 55.03; H, 4.74; F, 11.56; N, 5.53.

$^{13}$C NMR (100 MHz, CDCl$_3$): δ 176.4, 144.9, 143.3, 139.8, 138.2, 132.6, 129.9, 129.7, 129.4, 129.0, 127.9, 127.6, 127.0, 124.0, 123.7, 123.3, 120.6, 81.8, 50.8, 29.1, 25.6, 22.4, 13.7.

$^1$H NMR (400 MHz, CDCl$_3$): δ 7.44–7.10 (m, 8H), 5.93 (br s, 1H), 4.67 (br s, 1H), 4.28 (br s, 2H), 2.50 (br s, 2H), 22.30 (br s, 1H), 1.76–1.56 (m, 2H), 1.37–1.32 (m, 2H), 0.96–0.86 (m, 3H).

TLC: silica, 90:5:5 methylene chloride:methanol:acetic acid. R$_f$=0.64

EXAMPLE 3

2-Butyl-4-(trifluoromethyl)-1H-imidazole-5-carboxylic acid, ethyl ester

To a mixture of Example 1 (4.25 g, 15.00 mmol) and sodium acetate (15 g) in methanol (50 mL) and water (50 mL) at an ice bath temperature titanous chloride solution (50 mL of 20% solution) was added dropwise over 20 minutes with stirring After an hour at 0° C. the reaction mixture was warmed to room temperature and stirred for one hour. The reaction product was extracted with ethyl acetate (2×300 mL), the combined organic layer was washed with citric acid (100 mL of 5% solution) followed by aqueous sodium bicarbonate solution (100 mL), dried over magnesium sulfate and concentrated in vacuo to obtain pure Example 3 (3.42 g, 86% yield) as a solid.

Melting point: 51.0°–53.0° C.

$^1$H NMR (CDCl$_3$) d 4.50 (q, J=7.0 Hz, 2H), 2.89 (2 doublets, J=8.2 Hz, 2H), 1.84 (qn, J=8.2 Hz, 2H), 1.48 (m, 5H, sextet and triplet overlapped), 1.02 (t, J=7.0 Hz, 3H); $^{13}$C NMR (CDCl$_3$) d 159.2, 151.4, 135 (q, too peaks small to measure J value), 120.8 (q, J=268.0 Hz), 120.7, 61.8, 30.2, 27.9, 22.2, 13.7, 13.4; MS (M+H)+265.

EXAMPLE 4

2-Butyl-1-[[1-[2-(1H-tetrazol-5-yl)phenyl]-4-Indolyl]-methyl]-4-(trifluoromethyl)-1H-imidazole-5-carboxylic acid, ethyl ester A. 2-Butyl-1-[[1-(2-cyanophenyl)-1H-Indol-4-yl]methyl]-4-(trifluoromethyl)-1H -Imidazole-5-carboxylic acid, ethyl ester A mixture of Example 3 (470 mg, 1.78 mmol) and cesium carbonate (585 mg, 1.8 mmol) in dimethylformamide (4 mL) was stirred at room temperature for 15 minutes. To this reaction mixture was added 4-bromomethyl-1-(2-cyanophenyl)indole (555 mg, 1.78 mmol). The resulting mixture was stirred at room temperature for 3 hours. The solid was filtered and washed with ethyl acetate. The filtrate solution was concentrated in vacuo and the residue was purified by flash column chromatography (SiO$_2$, ethyl acetate:hexane 1:2) to obtain pure product compound A (870 mg, 98%) as an oil.

$^1$H NMR (CDCl$_3$) δ 7.95 (d, J=7.6 Hz, 1H), 7.85 (m, 1H), 7.69 (d, J=7.6 Hz, 1H), 7.63 (t, J=7.6 Hz, 1H), 7.58 (d, J=3.5 Hz, 1H), 7.35 (d, J=8.2 Hz, 1H), 7.24 (t, J=7.6 Hz, 1H), 6.85 (d, J=3.5 Hz, 1H), 6.48 (d, J=7.6 Hz, 1H), 6.01 (s, 2H), 4.35 (q, J=7.0 Hz, 2H), 2.78 (d.d, J=7.6 Hz, 2H), 1.76 (qn, J=7.6 Hz, 2H), 1.38 (sx, 2H), 1.35 (t, J=7.0, 3H), 0.94 (t, J=7.6 Hz, 3H);

$^{13}$C NMR (CDCl$_3$) δ 158.9, 152.7, 141.5, 136.2, 134.4, 133.9, 128.7, 128.5, 128.4, 127.8, 127.7, 127.5, 126.2, 123.1, 121.8, 121.6, 116.9, 116.2, 110.0, 109.9, 101.8, 61.7, 46.5, 29.57, 26.8, 22.3, 13.5 (Due to the size of the peaks , the carbons coupled with three fluorine atoms were not assigned precisely.); MS (M+H)+ 495.

B.
2-Butyl-1-[[1-[2-(1H-tetrazol-5-yl)phenyl]-4-indolyl]methyl]-4-(trifluoromethyl)-1H-imidazole-5-carboxylic acid ethyl ester A solution of compound A (800 mg, 1.62 mmol) and tri-n-butylin azide (1.88 g, 5.66 mmol) in xylene (5 mL) was stirred at 100°–110° C. for 24 hours. The reaction mixture was concentrated in vacuo and the residue was purified by preparative HPLC (column: YMC S-10 ODS, 50×500 mm; flow rate 105 mL/min.; mobile phase 78% aqueous methanol containing 0.1% trifluoroacetic acid; UV 254 nm). The fractions containing the desired product were combined and concentrated to obtain Example 4 (675 mg, 78% yield).

Melting point: 93.0°–95.0° C.

R$_f$=0.58 on silica gel TLC in ethyl acetate-acetic acid (100:1);

HPLC R$_t$=6.5 minutes at 254 nm; solvent system 78% aqueous methanol containing 0.2% phosphonic acid, 1.5 ml/min. flow rate in YMC S3-ODS column (6×150 mm).

$^1$H NMR (CDCl$_3$) δ 8.41 (m, 1H), 7.86 (m, 2H), 7.65 (m, 1H), 7.23 (m, 1H), 7.08 (m, 2H), 6.76 (m, 1H), 6.39 (d, J=6.5 Hz, 1H), 5.93 (br. s, 2H), 4.34 (q, J=7.6 Hz, 2H), 2.59 (t, bad resolution, 2H), 1.71 (qn, bad resolution, 2H), 1.37 (m, overlapped, 5H), 0.93 (t, J=7.6 Hz, 3H);

$^{13}$C NMR (CDCl$_3$) δ 159.2, 153.1, 136.9, 135.3, 132.8, 131.8, 129.7, 129.1, 128.5, 125.9, 123.78, 122.5, 121.5 (q, J=237 Hz, CF$_3$) 117.3, 110.2, 102.1, 62.0, 46.9, 30.1, 26.9, 22.7, 13.9; MS (M+1H$^+$ 538; IR (KBr) 1721 cm$^{-1}$.

Analysis for C$_{27}$H$_{26}$N$_7$F$_3$O$_2$.0.59 H$_2$O: Calc'd: C, 59.16; H, 5.00; N, 17.89; F, 10.60. Found: C, 59.40; H, 4.99; N, 17.65; F, 10.63.

What is claimed is:

1. A process for preparing a product of the formula

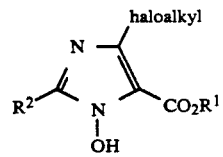

wherein:
R$^1$ is hydrogen, alkyl, haloalkyl, cycloalkyl, cycloalkylalkyl, aryl or aralkyl;
R$^2$ is alkyl, alkenyl, alkynyl, cycloalkyl, cycloalkylalkyl, cycloalkylalkenyl, cycloalkylalkynyl or —(CH$_2$)$_m$Z(CH$_2$)$_n$R$^3$, each of which is unsubstituted or substituted with 1 or 2 groups selected from halo and —CO$_2$R$^1$; or aryl or aralkyl, each of which is unsubstituted or substituted with 1 or 2 groups selected from halogen, lower alkoxy, lower alkyl and nitro;
R$^3$ is hydrogen, alkyl, cycloalkyl, lower alkenyl or lower alkynyl;
Z is O, NR$^4$ or S;
R$^4$ is hydrogen, alkyl, cycloalkyl, aryl, cycloalkylalkyl or aralkyl;
m is an integer from 0 to 5; and
n is an integer from 1 to 5;
and wherein the process comprises:
(a) reacting a ketone of the formula

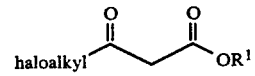

with a nitrogenic acid, nitrite or nitrate in the presence of an acid to form a hydroxyimino compound of the formula

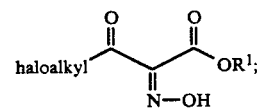

(b) reacting the hydroxyimino compound with an aldehyde of the formula

and an ammonium compound selected from ammonia, ammonium halide and ammonium hydroxide to form an N-hydroxyimidazole of the formula

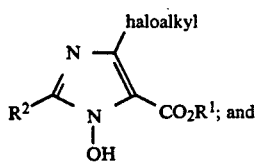

(c) reacting the N-hydroxyimidazole with a reducing agent selected
from titanium trichloride and zinc in the presence of a buffer to
form a product of the formula

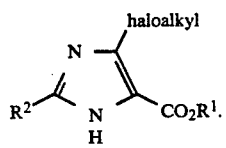

2. The process of claim 1, wherein haloalkyl is —CF$_3$ or —C$_2$F$_5$.
3. The process of claim 1, wherein R$^1$ is alkyl.
4. The process of claim 1, wherein R$^1$ is ethyl.
5. The process of claim 1, wherein R$^2$ is alkyl.
6. The process of claim 1, wherein R$^2$ is n-butyl.
7. The process of claim 1, wherein the nitrogenic acid, nitrite or nitrate is selected from nitric acid, alkali metal nitrite or alkali metal nitrate.
8. The process of claim 1, wherein the nitrogenic acid, nitrite or nitrate is sodium nitrite.
9. The process of claim 1, wherein the acid used in step (a) is acetic acid.
10. The process of claim 1, wherein the ammonium compound is ammonia.
11. The process of claim 1, wherein the reducing agent is titanium trichloride.
12. The process of claim 1, wherein the buffer is sodium acetate.
13. The process of claim 1, wherein the hydroxyimino compound is reacted with the aldehyde and the ammonium in situ.
14. A process for preparing a product of the formula

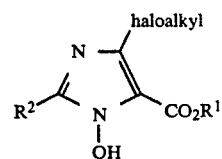

wherein:
R$^1$ is hydrogen, alkyl, haloalkyl, cycloalkyl, cycloalkylalkyl, aryl or aralkyl;
R$^2$ is alkyl, alkenyl, alkynyl, cycloalkyl, cycloalkylalkyl, cycloalkylalkenyl, cycloalkylalkynyl or —(CH$_2$)$_m$Z(CH$_2$)$_n$R$^3$, each of which is unsubstituted or substituted with 1 or 2 groups selected from halo and —CO$_2$R$^1$; or aryl or aralkyl, each of which is unsubstituted or substituted with 1 or 2 groups selected from halogen, lower alkoxy, lower alkyl and nitro;

R$^3$ is hydrogen, alkyl, cycloalkyl, lower alkenyl or lower alkynyl;
Z is O, NR$^4$ or S;
R$^4$ is hydrogen, alkyl, cycloalkyl, aryl, cycloalkylalkyl or aralkyl;
m is an integer from 0 to 5; and
n is an integer from 1 to 5;
and wherein the process comprises:
step (a) reacting a ketone of the formula

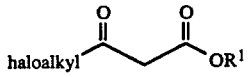

with a nitrogenic acid, nitrite or nitrate in the presence of an acid to form a hydroxyimino compound of the formula

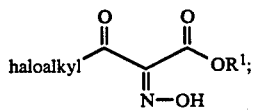

step (b) reacting the hydroxyimino compound with an aldehyde of the formula

R$^2$—CHO and an ammonium compound selected from ammonia, ammonium halide and ammonium hydroxide to form an N-hydroxyimidazole of the formula

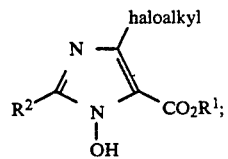

and further comprising
step (c) reacting the N-hydroxyimidazole from step (b) with a reducing agent selected from titanium trichloride and zinc in the presence of a buffer to form a product of the formula

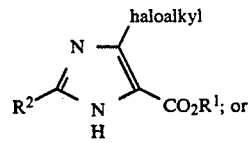

step (d) reacting the N-hydroxyimidazole from step (b) with

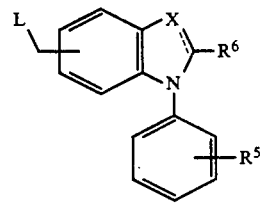

in the presence of a coupling agent in an organic solvent to form a product of the formula

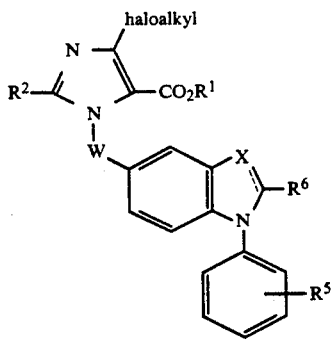

wherein:
L is halogen;
W is —CH₂— or —O—CH₂—;
X is N,

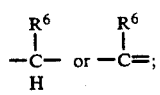

R⁵ is hydrogen

—NHSO₂-haloalkyl, —COOCH(R⁷)—OCR⁸, —CR⁹,
         ‖    ‖
         O    O

—OS(O)—OH, —SO₃H, —C(haloalkyl)₂OH, —O—P(O)—OH,
    |                                      |
    OH                                     OH —PO₃H, —NHP(O)—OH, —NHSO₂-haloalkyl,
           |
           OH

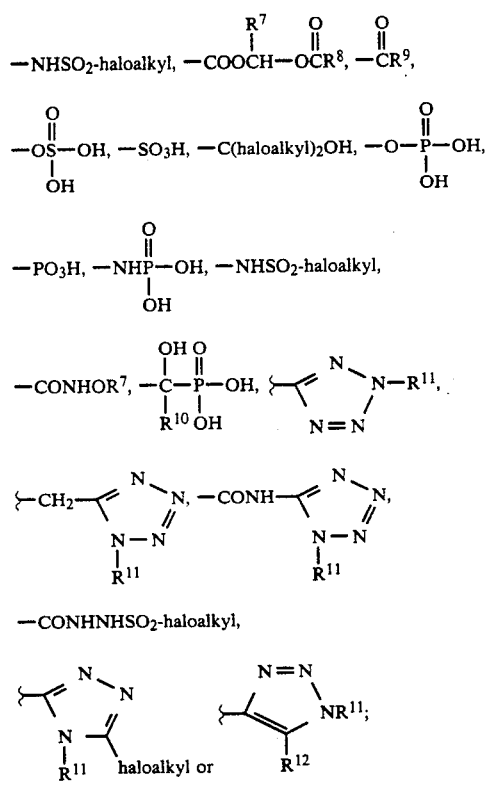

—CONHNHSO₂-haloalkyl,

R⁶ is hydrogen, halogen, haloalkyl, alkyl, aryl, cycloalkyl, cycloalkylalkyl, aralkyl or

—CR⁹;

R⁷ is hydrogen, alkyl, aryl, aralkyl, cycloalkyl or cycloalkylalkyl;
R⁸ is alkyl, —NR¹³R¹⁴ or

NH₂
          |
—CH—CH₂CO₂R¹;

R⁹ is hydrogen, cycloalkyl, —(CH₂)ₚC₆H₅, —OR¹¹ or —NR¹⁵R¹⁶;
R¹⁰ is hydrogen, alkyl or phenyl;
R¹¹ is hydrogen, alkyl, cycloalkyl, aryl, aralkyl, a 5- to 7-membered carbocyclic ring that may have another 5- to 7-membered carbocyclic ring fused thereto,

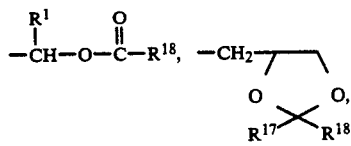

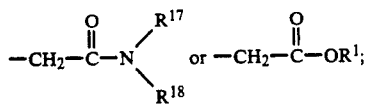

R¹² is —CN, —NO₂ or —CO₂R¹;
R¹³ and R¹⁴ are independently hydrogen, benzyl or together are alkylene or alkenylene, forming a 4- to 7-membered saturated, unsaturated or aromatic ring with the nitrogen atom to which they are attached;
R¹⁵ and R¹⁶ independently are hydrogen, alkyl, phenyl, benzyl, α-methylbenzyl or together with the nitrogen atom to which they are attached form a ring of the formula

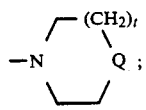

Q is NR⁷, O or CH₂;
R¹⁷ is hydrogen, alkyl, cycloalkyl, aryl or arylalkyl and R¹⁸ is hydrogen, alkyl, cycloalkyl, aryl, arylalkyl or alkoxy, or together R¹⁷ and R¹⁸ are —(CH₂)₂—, —(CH₂)₃—, —CH=CH— or

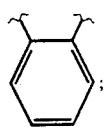

and
t is 0 or 1; or
step (c) and step (d);
and "coupling agent" refers to an alkali metal disilazane, carbonate or bicarbonate.

15. The process of claim 14, further comprising reducing the product to form a product of the formula

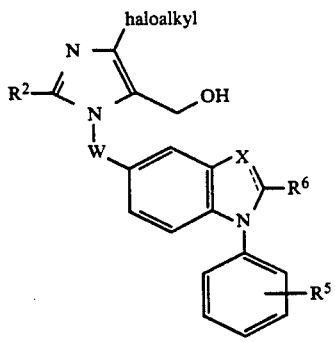

with a reducing agent selected from lithium aluminum hydride, lithium bis(ethoxymethoxy)aluminum hydride, lithium borohydride, sodium borohydride and zinc borohydride.

16. The process of claim 15, further comprising alkylating or arylating the product to form a product of the formula

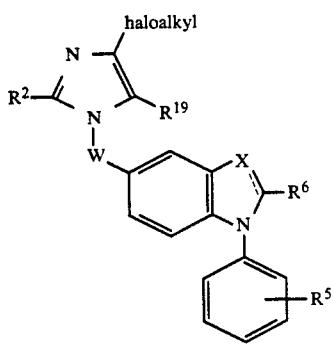

wherein:
R$^{19}$ is hydrogen; —CN; alkyl; haloalkyl; alkenyl; haloalkenyl; phenylalkenyl; —(CH$_2$)$_p$-imidazol-1-yl; —(CH$_2$)$_p$-1,2,3-triazolyl, unsubstituted or substituted with one or two groups selected from —CO$_2$R$^1$ and alkyl of 1 to 4 carbon atoms; —(CH$_2$)$_p$-tetrazolyl; —(CH$_2$)$_q$OR$^{20}$ other than —CH$_2$OH,

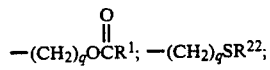

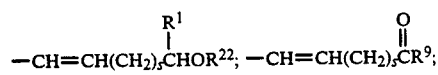

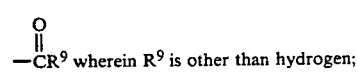

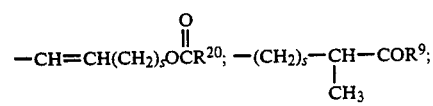

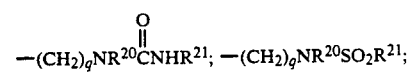

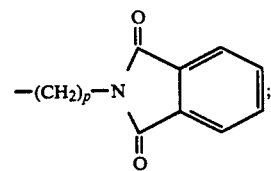

R$^{20}$ is hydrogen, alkyl, cycloalkyl, phenyl, or benzyl;
R$^{21}$ is alkyl, haloalkyl, 1-adamantyl, 1-naphthyl, 1-(1-naphthyl)ethyl, or —(CH$_2$)$_p$C$_6$H$_5$;
R$^{22}$ is hydrogen, alkyl, phenyl, benzyl, acyl, or phenacyl;
Y is O or S;
p is an integer from 1 to 10;
q is an integer from 1 to 10; and
s is an integer from 0 to 5.

17. The process of claim 14, further comprising subjecting the product to Wittig homologation to form a product of the formula

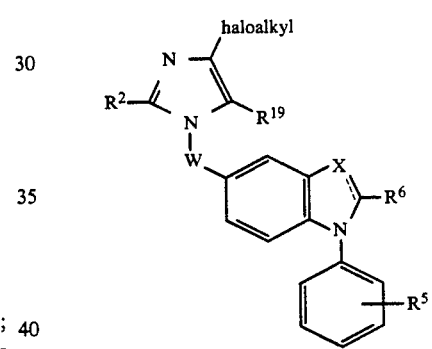

wherein:
R$^{19}$ is hydrogen; —CN; alkyl; haloalkyl; alkenyl; haloalkenyl; phenylalkenyl; —(CH$_2$)$_p$-imidazol-1-yl; —(CH$_2$)$_p$-1,2,3-triazolyl, unsubstituted or substituted with one or two groups selected from CO$_2$R$^1$ or alkyl of 1 to 4 carbon atoms; —(CH$_2$)$_p$-tetrazolyl; —(CH$_2$)$_q$OR$^{20}$ other than —CH$_2$OH,

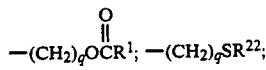

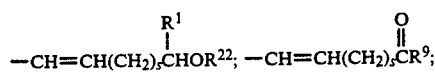

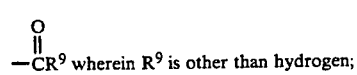

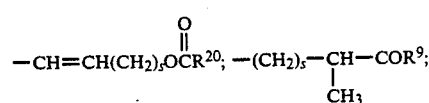

-continued

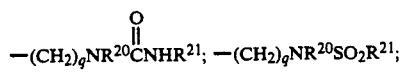

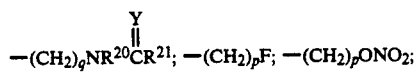

—(CH$_2$)$_p$N$_3$; —(CH$_2$)$_p$NO$_2$; or

-continued

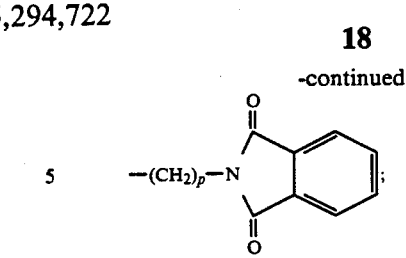

R$^{20}$ is hydrogen, alkyl, cycloalkyl, phenyl, or benzyl;
R$^{21}$ is alkyl, haloalkyl, 1-adamantyl, 1-naphthyl, 1-(1-naphthyl)ethyl, or —(CH$_2$)$_p$C$_6$H$_5$;
R$^{22}$ is hydrogen, alkyl, phenyl, benzyl, acyl, or phenacyl;
Y is O or S;
p is an integer from 1 to 10;
q is an integer from 1 to 10; and
s is an integer from 0 to 5.

18. The process of claim 14, wherein the coupling agent is potassium hexamethyldisilazane.

19. The process of claim 16, wherein the coupling agent is potassium hexamethyldisilazane.

* * * * *